United States Patent [19]

Oishi et al.

[11] Patent Number: 4,718,763
[45] Date of Patent: Jan. 12, 1988

[54] ATOMIC ABSORPTION SPECTROPHOTOMETER

[75] Inventors: Kounosuke Oishi, Mito; Masataka Koga; Kazuo Yasuda, both of Katsuta, all of Japan

[73] Assignee: Hitachi, Ltd., Tokyo, Japan

[21] Appl. No.: 848,460

[22] Filed: Apr. 7, 1986

[30] Foreign Application Priority Data

Apr. 8, 1985 [JP] Japan .................................. 60-73813

[51] Int. Cl.$^4$ .......................... G01N 21/72; G01J 3/42
[52] U.S. Cl. ...................................... 356/326; 356/315
[58] Field of Search ............... 356/307, 311, 312, 315, 356/316, 319, 326, 328

[56] References Cited

U.S. PATENT DOCUMENTS

| Re. 32,022 | 11/1985 | Parker et al. | 356/312 |
| 3,676,004 | 7/1972 | Prugger et al. | 356/320 |
| 3,811,778 | 5/1974 | Hadeishi | 356/312 |
| 4,035,083 | 7/1977 | Kleodriff et al. | 356/307 |
| 4,377,342 | 3/1983 | Koizumi et al. | 356/307 |
| 4,449,820 | 5/1984 | Koizumi et al. | 356/307 |

Primary Examiner—F. L. Evans
Attorney, Agent, or Firm—Antonelli, Terry, & Wands

[57] ABSTRACT

There is provided an atomic absorption spectrophotometer wherein a magnetic field having a suitable value is applied to a light source radiating the emission spectral light of the atom to be analyzed in the advance direction of the radiated light in order to cause the Zeeman effect so that the wavenumber of a component which is included in the spectra shifted in wavenumber and which is varied to have a smaller wavenumber may coincide with or approach the wavenumber whereat the absorption spectrum is maximized, thereby the sensitivity of the atomic absorption being raised, the linear region of the working curve being improved, and the emission spectral light being stabilized.

4 Claims, 9 Drawing Figures

ATOMIC ABSORPTION SPECTROPHOTOMETER

BACKGROUND OF THE INVENTION

The present invention relates to an atomic absorption spectrophotometer, and in particular to an atomic absorption spectrophotometer having an improved emission spectral distribution of a light source.

Figure 1:
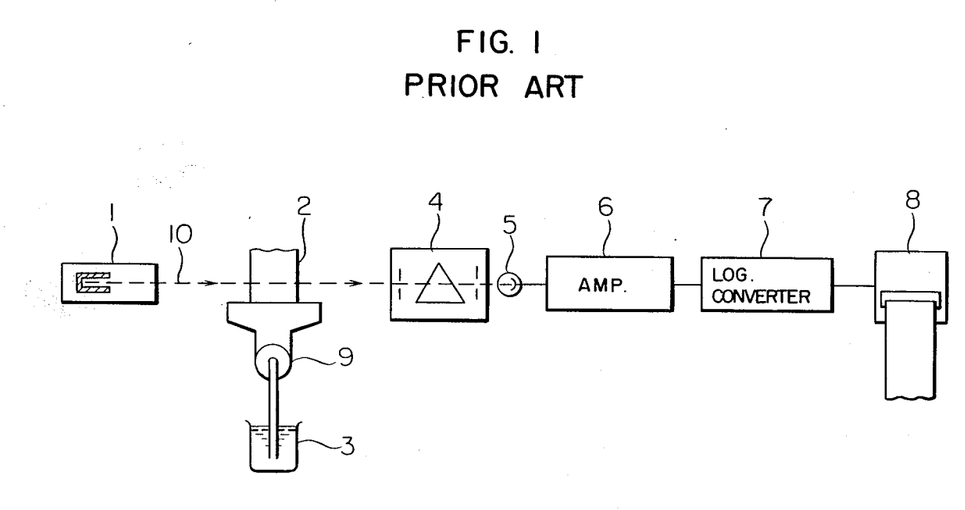
FIG. 1 shows configuration of an example of an atomic absorption spectrophotometer of the prior art.

FIG. 1 shows an example of an atomic absorption spectrophotometer of the prior art. A light ray 10 emitted by a light source 1 passes through an acetylene flame 2 and enters a spectroscope 4. The spectroscope 4 selects the wavelength of the atomic absorption line of the element to be analyzed. Only the light ray having this wavelength is received by a photoelectric conversion element 5. The photoelectric conversion element 5 is connected to an amplifier 6, which in turn is connected to a logarithmic conversion element 7. The output of the logarithmic conversion element 7 is supplied to an output indicator 8 to indicate the electric signal thus converted logarithmically. An analysis sample 3 of a water solution is turned into a spray with air by a nebulizer 9 and led into an acetylene flame 2. This spray is evaporated in the acetylene flame 2. Inorganic substances dissolved in the analysis sample of the water solution 3 are thermally resolved in the acetylene flame 2 of approximately 4200° C. to generate atom vapor. When the element to be analyzed is calcium (Ca), for example, a lamp such as a hollow-cathode lamp emitting a light ray of 422.67 nm in wavelength, which is the atomic spectral line of calcium is used as the light source 1. The wavelength of the absorption line of the atom to be analyzed which is generated in the acetylene flame 2 is also 422.67 nm. Matching in wavelength causes so-called resonance atomic absorption phenomenon. When the light ray 10 emitted from the light source 1 passes through the acetylene flame 2, therefore, the light having the wavelength of 422.67 nm is absorbed by calcium atoms existing in the acetylene flame 2.

Principle of Measurement

Assuming that $I_0$ = intensity of light (422.67 nm) of calcium atoms emitted from the light source $I$ = intensity of light of calcium atoms after passing through the acetylene flame $n$ = density of calcium atoms contained in the acetylene flame (1/cm$^3$)

$l$ = length of the acetylene flame that the light passes (cm)

$k$ = absorption coefficient of calcium atoms, the well known Beer's law holds true as $$I = I_0 \cdot \exp[-n \cdot n \cdot l \cdot k] \quad (1)$$

If the value of the ratio ($I/I_0$) between electric signals varying in proportion to two light intensities is converted into a logarithm value, the value of $[-n \cdot l \cdot k]$ which is in proportion to the density n of the atoms to be analyzed is obtained as evident from equation (1). Since the density n of the atom in the acetylene flame is in proportion to the concentration (ppm) of the element to be analyzed in the analysis sample of water solution, it is eventually possible to derive the concentration (ppm) of calcium contained in the analysis sample of the water solution 3. The concentration is the final object of the measurement. In the apparatus of the prior art, however, the principle of deriving the concentration of the aimed element is based on the photometry method using the well known Beer's law expressed by equation (1). In equation (1), light intensities $I_0$ and I as well as the absorption coefficient k are functions of the wavenumber $\nu$ cm$^{-1}$ of the light. Therefore, equation (1) can be rewritten as $$I(\nu) = I_0(\nu) \cdot \exp[-n \cdot l \cdot k(\nu)]. \quad (2)$$

Since the wavenumber ($\nu$ cm$^{-1}$) can be related to the wavelength $\lambda$ (cm) as $$\lambda \cdot \nu = 1,$$

equation (2) can also be represented as a function of the wavelength. When it is defined that $n \cdot l \cdot k = A$, A is referred to as the "absorbance".

Figure 2:
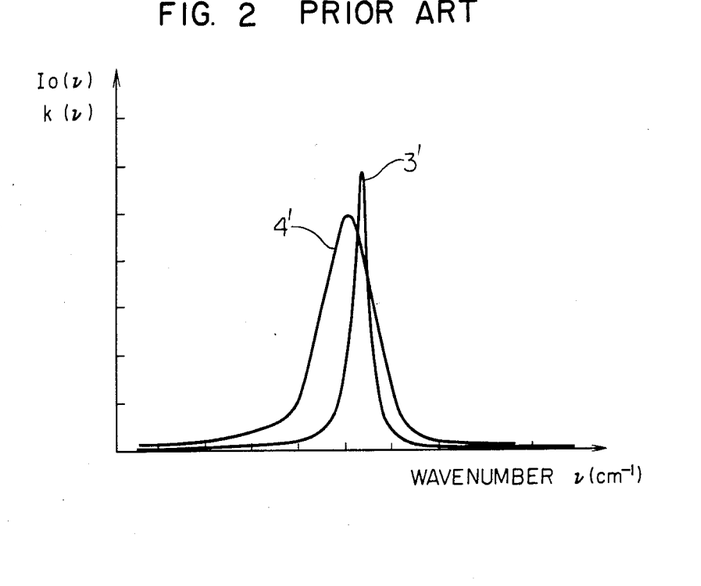
FIGS. 2 and 3 are graphs for illustrating drawbacks of the atomic absorption spectrophotometer of the prior art.

FIG. 2 shows the spectral distribution of incident light spectra $I_0(\nu)$ and absorption spectra $k(\nu)$ for the atomic spectra of calcium (Ca). The ordinate of FIG. 2 represents the values of the functions $I_0(\nu)$ and $k(\nu)$. The abscissa represents the wavenumber $\nu$(cm$^{-1}$). Curve 3' and 4' represent the spectral distribution of the functions $k(\nu)$ and $I_0(\nu)$, respectively. The wavenumber $\nu$(cm$^{-1}$) whereat the function $k(\nu)$ assumes the maximum value is shifted from that of the function $I_0(\nu)$ by $\Delta\nu$(cm$^{-1}$). As described in Wagenaar et al. "Spectrochimina Acta", Vol. 28B, Pages 157–173, 1972, this shift value depends upon the element and in general ranges from 0.01 to 0.08 cm$^{-1}$. For calcium, this shift is 0.037 cm$^{-1}$.

As well known by the above described literature written by Wagenaar et al., for example, the shift between the wavenumber whereat the emission spectrum $I_0(\nu)$ is maximized and the wavenumber whereat the absorption spectrum $k(\nu)$ of the same atom is maximized depends upon:

(1) kind of gas;
(2) pressure of gas; and
(3) temperature of gas wherein the calcium atoms are disposed. When the temperature and pressure of the atmospheric gas wherein the atoms are disposed are raised, the maximum values of $I_0(\nu)$ and $k(\nu)$ are displaced in such a direction as to decrease the wavenumber $\nu$ cm$^{-1}$.

Table 1 shows the difference in atmospheric gases wherein the calcium atoms are disposed in the apparatus of the prior art as illustrated in FIG. 1.

TABLE 1

Difference between atmospheric gas of light absorption atoms of calcium and that of emission atoms

| No. | Atmosphere | Spectral function | Kind of gas | Pressure of gas | Temperature of gas |
|---|---|---|---|---|---|
| 1 | Hollow-cathode lamp | $k(\nu)$ | Neon | 8 Torr. | 600° K. |
| 2 | Acetylene-air flame | $I_0(\nu)$ | Acetylene air | 760 Torr. | 2400° K. |

Table 1 shows the case of calcium atoms. In general, the gas enclosed in the hollow-cathode lamp of the prior art apparatus is neon (Ne) or argon (Ar), and its pressure ranges from 4 to 10 Torr. The temperature at the hollow cathode portion is raised as the discharge current (2 to 40 mA) is increased, and is in the range of 400° to 1200° K. The acetylene flame having absorption atoms therein is under the atmospheric pressure (760 Torr.). The temperature of the acetylene flame varies somewhat depending upon the flux of the air mixed with acetylene, and the temperature is in the range from 2200° to 2700° K. In every kind of analyzed element in the prior art apparatus of FIG. 1, the position on the axis of the wavenumber $\nu$ cm$^{-1}$ whereat the emission spectrum $I_0(\nu)$ of the light source 1 is maximized is always shifted in such a direction as to increase the wavenumber with respect to the position on the wavenumber axis whereat the absorption spectrum $k(\nu)$ of atoms in the acetylene flame 2 is maximized. This shift is in the range of approximately 0.01 to 0.08 cm$^{-1}$ This fact is also reported in the above described literature written by Wagenaar et al. in detail.

Figure 3:
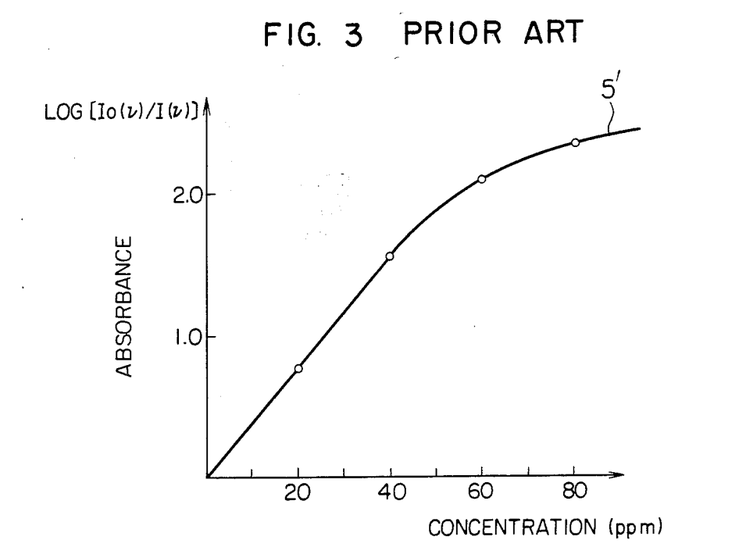

If the central wavenumber ($\nu$) of the spectral distribution of $I_0(\nu)$ does not match with that of $k(\nu)$ in equation (2), the absorption phenomenon appears in a section on the wavenumber axis wherein the emission spectrum and the absorption spectrum overlap each other. When the density of the atoms to be analyzed is low, absorption proportioned to the density is conducted on the overlapped wavenumber section. When the density becomes high, however, the emission spectra belonging to the overlapped wavenumber section are sufficiently absorbed to approach zero. Even if the density of the atoms to be analyzed is further raised, therefore, the amount of absorption no longer changes. Accordingly, a linear relationship does not hold true between the electrical signal $-\text{Log }[I(\nu)/I_0(\nu)]=\text{Log }[I_0(\nu)/I(\nu)]$ derived from the apparatus of FIG. 1 and the concentration C of the element to be analyzed. FIG. 3 shows a working curve 5' for the atomic absorption line (422.67 nm) of calcium (Ca) derived by using the prior art apparatus of FIG. 1. The working curve is a plot of the electrical signal Log $[I_0(\nu)/I(\nu)]$ (ordinate) as a function of the concentration C ppm of the element to be analyzed (abscissa). As evident from FIG. 3, the working curve 5' is warped as the concentration C ppm is increased. If the concentration C exceeds 80 ppm, the electrical signal Log $[I_0(\nu)/I(\nu)]$ scarcely increases. That is to say, the precision in measuring the concentration C is significantly lowered, the practical measurement being made impossible. This curve of the working curve depends upon the area of the overlapped wavenumber section between the emission spectrum and the absorption spectrum. Thus, the atomic absorption spectrophotometer of the prior art such as an example illustrated in FIG. 1 has a drawback that the working curve for every element to be analyzed is so warped toward the horizontal direction as to make measurement impossible for a concentration C ppm exceeding a certain value as illustrated in FIG. 3. Such a warp of the working curve is described in "Atomic absorption analysis" by Yasuda et al., pages 22-33, 1972.

If a magnetic field is applied to the light source, the emission spectrum line is separated according to the magnitude of the magnetic field and a wavenumber shift is caused. That is to say, the so-called Zeeman effect is caused as described in Harvey Elliot White, "INTRODUCTION TO ATOMIC SPECTRA", page 152, 1968, for example.

An attempt to raise the sensitivity of the atomic absorption by using the Zeeman effect is described in Schrenk et al., "SPECTROSCOPY LETTERS", 1(6), pages 237-244, 1968. That is to say, a magnetic field of 3400 Gauss is applied to a light source composed of a hollow-cathode lamp of iron Fe in a direction perpendicular to the direction of light emitted from the light source. This results in the raised sensitivity of the atomic absorption lines of elements to be analyzed other than Fe, i.e., manganese Mn, nickel Ni, and copper Cu. When this method is used, the radiation atomic spectrum of ion is disrupted into three components $\sigma^+$, $\sigma^-$ and $\pi$ by the Zeeman effect. Since all of these three components are used, the wave number whereat the emission spectral distribution $I_0(\pi)$ is maximized does not coincide with the wave number whereat the absorption spectral distribution $k_0(\nu)$. In addition, the linearity of the working curve has not been considered at all.

SUMMARY OF THE INVENTION

An object of the present invention is to provide an atomic absorption spectrophotometer which is free from the drawbacks of the prior art apparatus illustrated in FIG. 1, or an atomic absorption spectrophotometer which significantly reduces the restriction imposed upon the measurable concentration range resulting from the warp of the working curve illustrated in FIG. 3 or the warp of a curve showing the relation between the electrical signal Log $[I_0(\nu)/I(\nu)]$ and the concentration C of the analyzed element, caused by a shift between the emission spectrum $I_0(\nu)$ and the absorption spectrum $k(\nu)$.

Another object of the present invention is to provide an atomic absorption spectrophotometer in which stable light intensities of emission spectral light are available by stabilized discharge of a hollow-cathode lamp.

In an atomic absorption spectrophotometer used for quantitative analysis of extremely small quantities of various elements according to the present invention, therefore, a magnetic field having a suitable value is applied to a light source radiating the atomic spectrum of the atom to be analyzed, in parallel to the radiated light ray in order to cause the Zeeman effect so that the wavenumber whereat the light intensity of the $\sigma^-$ component which is included in the spectra shifted in wavenumber and which is varied to have a smaller wavenumber may coincide with or approach the wavenumber whereat the absorption of the absorption spectrum of the analyzed atom is maximized, thereby the sensitivity of the atomic absorption being raised, the linear region of the working curve being expanded, and eventually the measurable concentration range of the analyzed atom being expanded.

DESCRIPTION OF PREFERRED EMBODIMENTS

Figure 4:
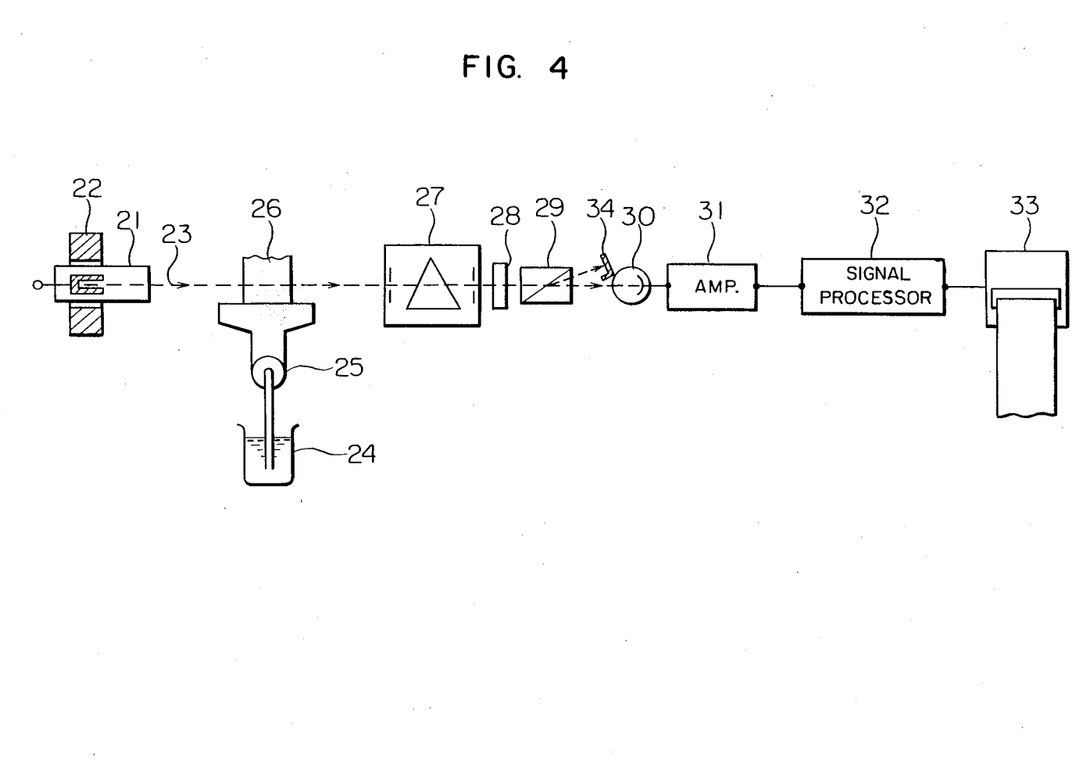
FIG. 4 shows configuration of an embodiment of an atomic absorption spectrophotometer according to the present invention.

FIG. 4 shows the configuration of an embodiment of an atomic absorption spectrophotometer according to the present invention. Reference numeral 21 denotes a light source for radiating the atomic spectra. Hollow-cathode discharge lamps are widely used for this purpose. Reference numeral 22 denotes a ring shaped magnet. The light source 21 is so inserted in the ring of the ring shaped magnet 22 that the direction of the magnetic field may be in parallel to the direction of the light ray 23 radiated from the light source 21.

An analysis sample 24 of water solution is sucked by a nebulizer 25 to be led into the acetylene flame 26 in the spray form. Water is evaporated and the dissolved inorganic substances are dissociated into atoms in the flame. In a section of wavenumber wherein the radiation spectra from the light source 22 and the absorption spectra of the atom generated in the acetylene flame 26 overlap each other, the light ray 23 is absorbed by the so-called atomic absorption phenomenon. In this case, the so-called Beer's law represented by equation (2) holds true between the density n ($1/cm^3$) of atoms existing in the acetylene flame 26, the intensity $I_0$ of the light ray 23, and the intensity I of the light ray passed through the acetylene flame 26. In addition, there is a fixed proportional relation between the density n of atoms in the acetylene flame 26 and the concentration C ppm of identical atoms in the analysis sample 24 of the water solution. The light having a wavelength of atomic absorption is selected by a spectroscope 27 to be applied to a retardation plate 28. The retardation plate 28 is used to convert the circularly polarized light into linearly polarized light.

When a magnetic field is applied to the light source 21 by the magnet 22, the atomic spectra emitted from the light source 21 are polarized into two circularly polarized components $\sigma^+$ and $\sigma^-$ by the Zeeman effect. These two circularly polarized components $\sigma^+$ and $\sigma^-$ are converted into two linearly polarized light components which are orthogonal each other by the retardation plate 28. Only the linearly polarized light among two lineary polarized light rays corresponding to the $\sigma^-$ component is passed through by a polarizer 29 to be applied to a photoelectric conversion element 30. The electrical signal is amplified by an amplifier 31 and converted into a logarithmic form to produce a difference signal in a signal processor 32. That is to say, an electrical signal corresponding to Log [$I_0$/I] is produced. This signal is displayed by a signal indication unit 33 each time the analysis sample is measured.

Figure 5:
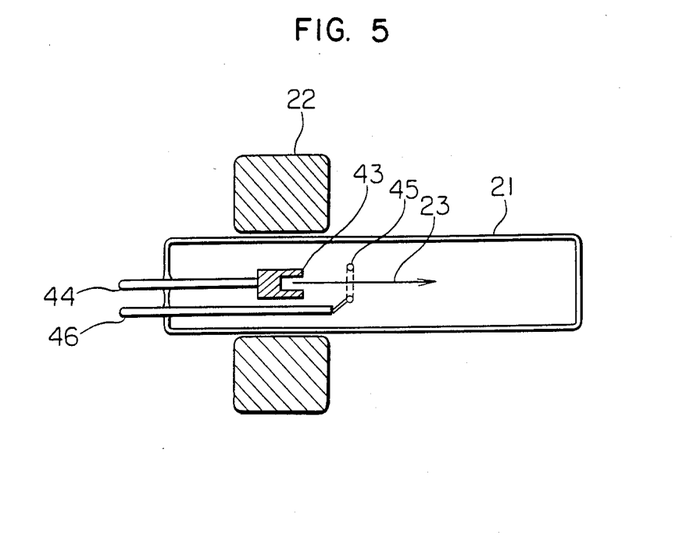
FIG. 5 shows configuration of an embodiment of a light source and its periphery of an atomic absorption spectrophotometer according to the present invention.
Figure 6:
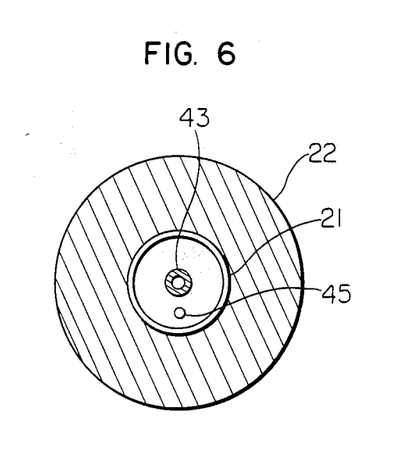
FIG. 6 is a view of FIG. 5 seen from the light ray radiation direction.

The light source 21 of FIG. 4, i.e., the hollowcathode lamp and the ring shaped magnet 22 are shown in FIG. 5. The view of the hollow-cathode lamp of FIG. 5 seen against the advance of the light is shown in FIG. 6. In FIGS. 5 and 6, the ring shaped magnet 22 is so disposed as to apply a magnetic field in the axis direction of a hollow cathode 43 of the light source 21, i.e., the running direction of the light 23. The magnet may be a permanent magnet or an electromagnet. When a permanent magnet is used, it is desirable to replace the magnet so as to produce a magnetic field of strength suitable to the changed element to be analyzed. When an electromagnet is used, a variable exciting power source may be used to adjust the strength of the magnetic field produced by the electro-magnet. Reference numeral 45 denotes an anode. Approximately 400 volts is supplied between an anode terminal 46 and a cathode terminal 44 to effect discharge and emit the light 23.

Figure 7:
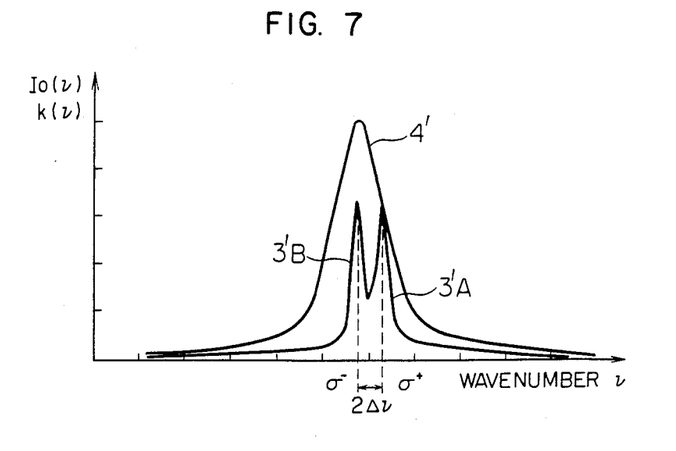
FIGS. 7 to 9 are graphs for showing effects of the atomic absorption spectrophotometer according to the present invention.

If a magnetic field of H gauss is applied to the lamp of FIG. 5 in the axis direction of the hollow cathode 43, i.e., in the advance direction of the atomic spectral light 23, the radiation spectrum 3' of FIG. 2, for example, is disrupted into two spectra 3'A and 3'B by the Zeeman effect as illustrated in FIG. 7. The ordinate of FIG. 7 represents the value of the emission spectrum $I_0(\nu)$ or the absorption spectrum $k(\nu)$. The abscissa represents the wavenumber $\nu cm^{-1}$. Among the emission spectra disrupted by the application of the magnetic field, 3'A denotes the component $\sigma^+$ and 3'B denotes the component $\sigma^-$. Reference numeral 4' denotes the absorption spectrum of the atom. The Zeeman effect and the spectrum disruption are described in the aforementioned reference by Harvey Elliot White, in detail.

As described before, the warp of the working curve 5' as illustrated in FIG. 3 depends upon the area of the overlap region between the emission spectral distribution $I_0(\nu)$ 3' and the absorption spectral distribution 4' as illustrated in FIG. 2.

If the emission spectrum 3' is subjected to the Zeeman disruption, to be shifted in wavenumber, therefore, the area of the overlap region between both spectra is increased, and hence the linearity of the working curve 5' as illustrated in FIG. 3 can be improved.

Figure 8:
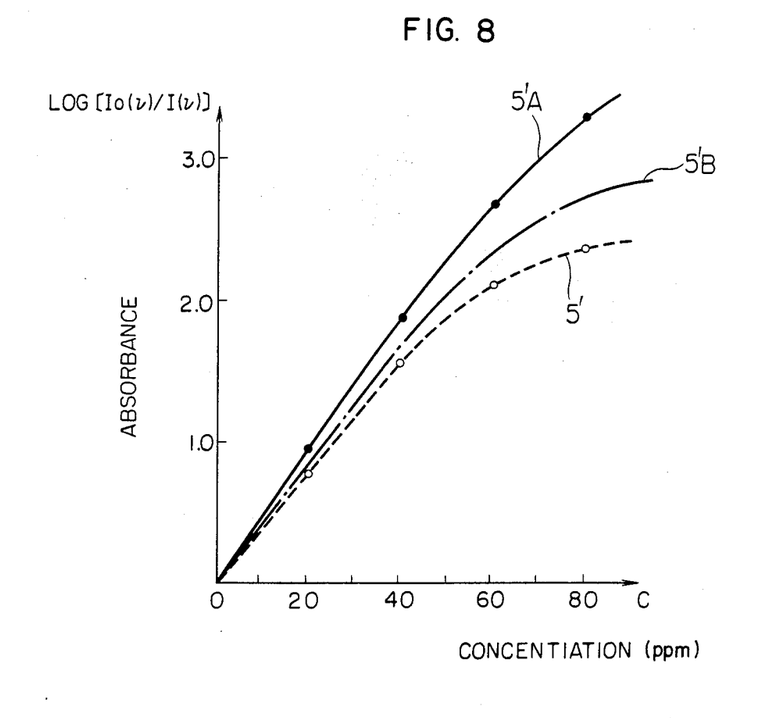

A broken line 5' of FIG. 8 is identical to the working curve 5' as illustrated in FIG. 3. It is evident from FIG. 8 that the linearity is improved as shown by a working curve 5'B when a magnetic field is applied to a hollow-cathode lamp having a emission spectrum of the atom to be analyzed in the advance direction of the light in accordance with the present invention.

Application of a magnetic field to a hollow-cathode lamp in the light radiation direction functions to narrow the discharge region between the cathode and anode of the hollow-cathode lamp. As a result, discharge and hence the emission spectral intensity is stabilized.

As described in the aforementioned literature by Hoda et al., equation (2) holds true for widely varied absorbance values (0.0 to 3.0) on condition that the wavenumber $\nu$ cm$^{-1}$ or wavelength whereat the spectral distribution function $I_0(\nu)$ is maximized agrees with that of $k(\nu)$.

Assuming that the disruption spacing between the $\sigma^+$ component 3'A and the $\sigma^-$ component 3'B caused by the Zeeman effect is $2\Delta\nu$ (cm$^{-1}$), it can be related to the strength H (Gauss) of the magnetic field as $$\Delta\nu = 4.67 \times 10^{-5} \times H \quad (3)$$

as described in the aforementioned literature by Harvey Elliot White.

As described with reference to FIG. 2 before, a shift is caused for the calcium spectrum, Ca 422.67 nm between the wavenumber whereat the absorption spectrum $k(\nu)$ of the atom is maximized and that whereat the emission spectrum $I_0(\nu)$ is maximized. The shifts is represented as $$\Delta\nu = 0.037 \text{ cm}^{-1}.$$

Figure 9:
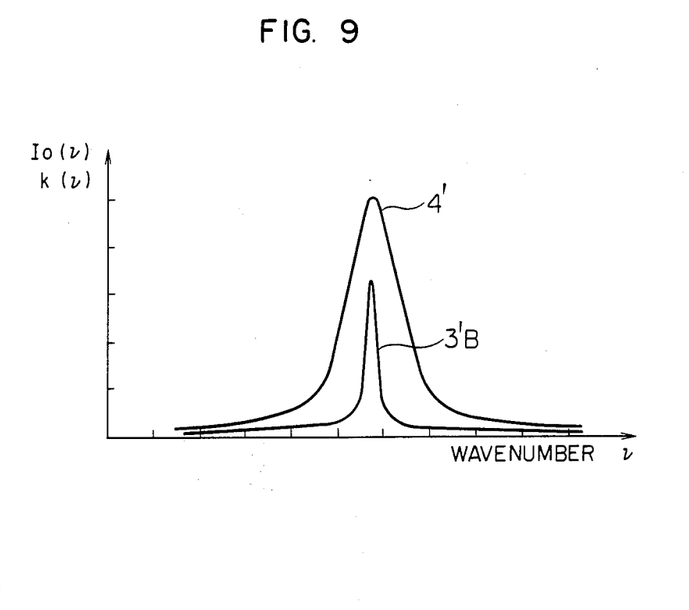

If the intensity H of the magnetic field generated by the ring shaped magnet 22 of FIG. 4 is defined as $$H = 790 \text{ Gauss},$$

it follows that $\Delta\nu = 0.037$ cm$^{-1}$ from equation (3). It is thus possible to square the wavenumber whereat the $\sigma^-$ component 3'B of the emission spectrum is maximized with the wavenumber whereat the absorption spectrum 4' is maximized. The $\sigma^+$ component 3'A is displaced from the $\sigma^-$ component 3'B by $2\Delta\nu=0.074$ cm$^{-1}$ in the direction wavenumber increase. The $\sigma^+$ component 3'A and $\sigma^-$ component 3'B are circularly polarized in the counterclockwise direction and in the clockwise direction with respect to the magnetic field direction, respectively. When passing through a suitable retardation plate, the components 3'A and 3'B are converted into two linearly polarized light rays which are orthogonal each other. Among the linearly polarized $\sigma^+$ component 3'A and $\sigma^-$ component 3'B applied to the polarizer 29 of FIG. 4, only the $\sigma^-$ component 3'B is passed through the polarizer 29 in the same direction as the incidence direction. The $\sigma^+$ component 3'A is changed in the transmission direction and interrupted by a screen 34. The $\sigma^+$ component 3'A is not incident onto the photoelectric conversion element 30. In the apparatus of FIG. 4, therefore, only the $\sigma^-$ component 3'B among two spectra disrupted by the Zeeman effect is applied to the amplifier 31 as an electrical signal. This state is shown in FIG. 9. In FIG. 9, the ordinate represents magnitude values of spectral intensy $I_0(\nu)$ and $k(\nu)$, and the abscissa represents the wavenumber $\nu$ cm$^{-1}$. The wavenumber whereat the $\sigma^-$ component 3'B of the Zeeman-disrupted spectrum is maximized agrees with the wavenumber whereat the absorption spectrum 4' is maximized. In this case, a condition for equations (1) and (2) to hold true for values of absorbance A exceeding 2.0 is satisfied. That is to say, the condition that the peak of the emission spectrum agrees with that of the absorption spectrum in wavenumber is satisfied. A curve 5'A of FIG. 8 is a working curve for an atomic absorption line (422.67 nm) of calcium (Ca) when the emission spectrum is made to agree with the absorption spectrum in the present invention apparatus of FIG. 4. That is to say, the curve 5'A shows the relation between the electrical signal Log $[I_0(\nu)/I(\nu)]$ and the concentration C (ppm) of calcium at that time. Effect of the present invention are made clear by comparing the working curve 5'A of the present invention with the working curve of the prior art as follows.

(1) The linear region of the working curve is expanded by 1.5 times.
(2) The ratio of the signal Log $[I_0(\nu)/I(\sigma)]$ to the concentration C, i.e., the tangent of the curve is increased by 1.2 times. The sensitivity is raised by 1.2 times.

Table 2 shows the intensity of the magnetic field which should be applied to the hollow-cathode lamp constituting the light source 23 by the magnet 22 in the embodiment of an apparatus according to the present invention as illustrated in FIG. 4, on the condition that the wavenumber $\nu$ (cm$^{-1}$) whereat the $\sigma^-$ component 3'B included in the Zeeman-disrupted emission spectrum is maximized agrees with the wavenumber whereat the absorption spectrum is maximized.

TABLE 2

Intensity of magnetic field for various spectra

| Element | Wavelength nm | Wavenumber cm$^{-1}$ | Magnetic field Gauss |
|---|---|---|---|
| Al | 396.1 | 0.048 | 1030 |
| Ca | 422.7 | 0.037 | 790 |
| Cr | 425.4 | 0.014 | 300 |
| Ga | 403.3 | 0.045 | 960 |
| In | 410.2 | 0.040 | 860 |
| K | 404.4 | 0.063 | 1350 |
| K | 404.7 | 0.072 | 1540 |
| Mn | 403.1 | 0.014 | 300 |
| Mo | 390.3 | 0.020 | 430 |
| Ti | 398.2 | 0.026 | 560 |

(Note)
The value of wavenumber for each wavelength of element is cited from the aforementioned literature of Wagenaar et al.

It is understood from Table 2 that the range the intensity (H Gauss) of magnetic field for atomic absorption lines of nine representative elements may assume can be represented as $$300 \leq H \leq 1540. \tag{5}$$

We claim:

1. An atomic absorption spectrophotometer comprising:
   means for atomizing a sample;
   a light source for emitting an emission spectral light ray of an atom to be analyzed toward said sample atomized by said atomizing means;
   magnet means for supplying a magnetic field to said light source to cause the Zeeman effect, said magnet means including means for supplying said light source with a magnetic field having such a magnitude as to generate an emission spectrum having a peak at a wavenumber substantially equal to the wavenumber whereat the absorption spectrum of said atom to be analyzed is maximized;
   means for measuring the intensity of the atomic spectrum of said atom to be analyzed which has been transmitted through said atomized sample so as to enable expansion of the linear range of a working curve of absorbance versus concentration; and
   means for determining the absorbance of said atom to be analyzed in accordance with the working curve on the basis of the measurement reults by said measuring means.

2. An atomic absorption spectrophotometer according to claim 1, wherein said magnet means includes means for supplying a magnetic field in the substantially same direction as the advance direction of the light radiated from said light source.

3. An atomic absorption spectrophotometer according to claim 1, wherein said measuring means includes means for measuring only the wavenumber section around the maximum of said absorption spectrum.

4. An atomic absorption spectrophotometer according to claim 1, wherein said magnet means enables shifting of the wavenumber of the emission spectrum so as to increase an area of an overlap region between the emission spectrum and the absorption spectrum, said measuring means effecting measurement in the area of the overlap region whereat the absorption spectrum of said atom to be analyzed is maximized for enabling expansion of the linear region of the working curve.

* * * * *